United States Patent [19]

Scott

[11] 3,932,614

[45] Jan. 13, 1976

[54] METHOD OF LUBRICATING OR SOFTENING THE SKIN

[75] Inventor: Howard L. Scott, Philadelphia, Pa.

[73] Assignees: Fabalon, Inc.; K. & W. Scott Trust; C. N. Wragg, Jr.; B. Wragg, all of Philadelphia, Pa. ; part interest to each

[22] Filed: Oct. 21, 1974

[21] Appl. No.: 516,817

Related U.S. Application Data

[63] Continuation-in-part of Ser. No. 230,487, Feb. 2, 1972, abandoned.

[52] U.S. Cl. ............... 424/78; 424/64; 424/69; 424/73; 424/81
[51] Int. Cl.² ............... A61K 7/00; A61K 7/025; A61K 7/035; A61K 31/74
[58] Field of Search ............ 424/64, 73, 78, 69, 70, 424/71, 81, 82, 83; 264/127; 252/522

[56] References Cited

UNITED STATES PATENTS

| | | | |
|---|---|---|---|
| 3,275,561 | 9/1966 | Pye | 424/73 |
| 3,340,152 | 9/1967 | Hotko | 264/127 |
| 3,568,685 | 3/1971 | Scott | 424/71 |

*Primary Examiner*—Albert T. Meyers
*Assistant Examiner*—A. P. Fagelson
*Attorney, Agent, or Firm*—Arthur A. Jacobs, Esq.

[57] ABSTRACT

The method of lubricating or softening the skin comprising the application of cosmetic preparations such as ointments, salves, creams, lotions, bar soaps, and the like, that contain a durable dry lubricant, comprising perfluorocarbon resins, said lubricant being inert to human and animal skin tissue, nonagglomerative, and sized to fit smoothly within the crease lines of human and animal skin tissue.

2 Claims, No Drawings

METHOD OF LUBRICATING OR SOFTENING THE SKIN

This application is a continuation-in-part of co-pending Serial No. 230,487, filed February 2, 1972, now abandoned.

The present invention relates to the manufacture of cosmetic preparations, and more particularly to the preparation of cosmetic ointments, salves, creams, lotions and the like that contain artificial and durable dry lubricants that are inert to the human and animal skin tissue, nonagglomerative, and sized to fit smoothly within the crease lines of human and animal skin tissue.

This invention further relates to the preparation of cosmetic compositions employing as a base, or base adjuvant, micron size dry lubricants that have higher emolliency and smoother characteristics than those hitherto available.

There has been great demand for a durable satisfactory base for use in the manufacture of cosmetic preparations accpetable for use on the skin. Heretofore, the most commonly used bases for this purpose have been lanolin, mink oil, petrolatum and the like. However, extensive uses of these substances as bases, or constituents of bases of ointments, salves and creams have shown that they are not satisfactory because of the marked tendency of these materials to leave greasy, sticky and sometimes odorous oil on the skin. Furthermore, they are not durable. In this respect, lanolin has not been entirely satisfactory because of its effect on those having allergic reactions thereto. Petrolatum has not been found satisfactory in the cosmetics because it is relatively incompatible with aqueous materials which are generally incorporated in or used with cosmetic preparations. Furthermore, petrolatum is not readily absorbed by the skin and hence is not particularly efficient in distributing a medicament which may be contained in the ointment, salve or lotion throughout the affected area on the skin.

It is the principal object of the present invention to provide a base, or base adjuvant, for the manufacture of cosmetics of the type mentioned above which combines a high degree of skin protection with emolliency, is exceptionally stable and is substantially greaseless and is durable.

Other objects of the present invention will be apparent from the following specification and claims.

In accordance with the present invention, it has now been found that cosmetic preparations such as cold creams, vanishing creams, rouge, lipsticks, protective creams, etc., containing a durable inert, dry lubricant, in a proportion of about 1% to about 50% by weight, combines a high degree of skin protection with emolliency, are exceptionally stable, are substantially greaseless, and are very durable. As a result, ointments, salves, creams and the like, which are prepared from bases containing such lubricant have skin softening and coating characteristics which are substantially greater than those imparted by other animal or vegetable oils and fats. They are also, suprisingly, more stable to atmospheric conditions than compositions prepared from more conventional bases, are substantially odorless, and do not become rancid.

As indicated above, a base oil or adjuvant in cosmetic preparations should be stable at atmospheric conditions, free of greasy or sticky effects, non-toxic and inert to the body skin and not susceptible to rancidity. A micron size dry powered lubricant, and particularly a resinous perfluorocarbon, having a particle size of about 0.01 to about 30 microns, and preferably a particle size of about 0.01 to about 0.5 microns, has been found to possess these characteristics to a substantially higher degree than the animal or vegetable fats and oil hitherto used for this purpose.

Perfluorocarbon resins within the scope of this invention include the homopolymer of tetrafluoroethylene, the homopolymer of hexafluoropropylene, and the copolymer of tetrafluoroethylene and hexafluoropropylene having the formula $-(CF_2CF_2-CF_2CFCF_3)_n-$.

These perfluorocarbon resins have a molecular weight of between about 1,000,000 to about 10,000,000, a viscosity greater than $10^{10}$ poises at 380°C, a specific gravity of about 2.18–2.24, and a melting point of over 600°F.

These resins will not lump or agglomerate either in solutions or on the skin, are generally inert to the actions of body chemistry, whereby they will neither react to body temperature nor break down due to the moisture of the body.

Chlorotrifluoroethylene resins have also been found to be advantageously used in making the dry lubricant type of cosmetics.

In order to compare the surface tension of products within the scope of the present invention with lubricants customarily used in cosmetics, a formulation was prepared wherein 3% of the homopolymer of tetrafluoroethylene, having a particle size of 4–18 microns, was suspended in a thickening agent of carboxypolymethylene with which it was mixed at room temperature. The surface tension of the resultant gel was then compared with the following selected vegetable and animal oils, using a DuNuby Tensiometer at 26°C, with the following results:

| | |
|---|---|
| Petrolatum | Semi-solid |
| Lard | Semi-solid |
| Lanolin | Semi-solid |
| Corn Oil | 36.8 |
| Neatfoot Oil | 35.9 |
| Mink Oil | 34.1 |
| Sweet Almond Oil | 33.8 |
| Gelled homopolymer of tetrafluoroethylene | 27.5 |

The above data show that the perfluorocarbon resin has a lower surface tension than that of the animal oils and fats customarily employed in cosmetics.

Skin texture, feel, tone and touch were tested by placing an amount of gelled cosmetic preparation containing an effective amount of the perfluorocarbon resin and a similar preparation containing an equal amount of lanolin on separate skin areas. The preparation containing the resin was absorbed almost immediately leaving behind a soft texture, and the skin was smooth to the touch. After 35 minutes, the lanolin that was placed on the skin was sticky, greasy, and spotty.

The following examples are illustrative of compositions containing effective amounts of powdered resin. In each example the particle size of the resin is about 0.05 to 0.5 micron. Although various of these examples include other lubricants such as lanolin, petrolatum or oil, much less of these other lubricants are used than would otherwise be necessary. From these examples it will be evident to those skilled in the art that a large number of cosmetic preparations could be prepared in a similar manner.

EXAMPLE 1

Protective Cream:

| Components | Parts by Weight |
|---|---|
| Stearic acid | 8.0 |
| Petrolatum | 6.0 |
| Glycerin | 3.0 |
| Glyceryl monostearate | 6.0 |
| Triethanolamine | 1.5 |
| Water | 56.0 |
| Lanolin (anhydrous) | 7.5 |
| Talc | 8.0 |
| Copolymer of tetrafluoroethylene and hexafluoropropylene | 2.0 |
| Perfume qs | |
| | 100% |

Mix ingredients and warm to 85° to 95°C. When dissolved, stir until almost cool. Add perfume and stir well, or pass through homogenizer. The selected resins may be varied from 1% to 15% without materially affecting the consistency.

EXAMPLE 2

Hand Lotion:

| Components | Parts by Weight |
|---|---|
| Propylene glycol | 2.0 |
| Petrolatum | 3.0 |
| Stearic acid | 6.0 |
| Triethanolamine | 1.0 |
| Glycerin | 2.0 |
| Homopolymer of hexafluoropropylene | 2.0 |
| Water | 83.0 |
| Perfume, qs | |
| | 100% |

Mix and warm all ingredients to 75° to 85°C. Stir the melted mixture until cool. Add the perfume if desired. The selected resins may be varied from 0.5% to 12% in this preparation without affecting the consistency.

EXAMPLE 3

Cold Cream:

| Components | Parts by Weight |
|---|---|
| Propylene glycol monostearate | 4.0 |
| Lanolin (anhydrous) | 6.0 |
| Mineral Oil | 26.0 |
| Triethanolamine | 1.5 |
| Homopolymer of tetrafluoroethylene | 4.5 |
| Water | 58.0 |
| Perfume, qs | |
| | 100% |

Warm all ingredients except the perfume in a stainless container at 75°C. Remove from heat and stir until mixture is almost at room temperature. Incorporate perfume and stir until cool. The selected resins may be varied from 0.5% to 17% by replacing an equal quantity of mineral oil.

EXAMPLE 4

Lipstick:

| Components | Parts by Weight |
|---|---|
| Beeswax | 38.0 |
| Vegetable Oil | 32.0 |
| Cocoa Butter | 16.0 |
| Lanolin (anhydrous) | 5.0 |
| Homopolymer of tetrafluoroethylene | 4.0 |
| Mineral Oil | 5.0 |
| Perfume, qs | |
| | 100% |

The selected resins content may be varied from 1% to 11%. To this base may be added the usual coloring agents. The material may be put through a colloid or roller mill and shaped into the ordinary lipstick form. Also the above preparation may contain perfume and if desired, antioxidants and preservative, such as methyl and propyl Parasept, nordihydroguaiaretic acid, and the like in the amounts of 0.01% to 15.0%.

EXAMPLE 5

Ointment:

| Components | Parts by Weight |
|---|---|
| Water | 75.0 |
| Carboxypolymethylene | .8 |
| Sodium Hydroxide (10% solution) | 3.2 |
| Homopolymer of hexafluoropropylene | 16.0 |
| | 100% |

Carefully disperse the Carboxypolymethylene in the water. After dispersion is complete add the sodium hydroxide with slow speed agitation to prevent excessive inclusion of air. Add the perfluorocarbon resin in the same manner. Mix to homogeneity. A sample prepared in this fashion has a viscosity of 60,000cps (Brookfield, 20rpm) and a pH of 7.1

EXAMPLE 6

Brushless Shaving Cream:

| | Components | Parts by Weight |
|---|---|---|
| Part A: | Mineral Oil | 95.7 |
| | Lanolin | 4.2 |
| | Stearic acid | 143.0 |
| Part B: | Water | 669.0 |
| | Carboxypolymethylene | 5.0 |
| | Homopolymer of tetrafluoroethylene | 50.0 |
| | Triethanolamine | 33.8 |
| | Perfume, qs | |

Form B by carefully dispersing the carboxypolymethylene in the water then adding the triethanolamine. Heat both A. and B. to 75°C and add A. & B. with vigorous agitation. Mix this uniformly and then cool it rapidly to 30°C. Add perfume when the temperature is about 50°C. This cream has a pH of 7.0 and a viscosity of 35,000cps (Brookfield, 20rpm). This cream works well in giving a closer, smoother more comfortable shave.

EXAMPLE 7

Cleansing Cream:

| | Components | Parts by Weight |
|---|---|---|
| Part A: | Beeswax | 80.0 |
| | Light Mineral Oil | 490.0 |
| | Paraffin | 70.0 |
| | Cetyl Alcohol | 10 |
| | Triethanolamine | 10 |
| Part B: | Water | 300.00 |
| | Chlorotrifluoroethylene resin | 38 |
| | Carboxypolymethylene | 2 |
| | Perfume, qs | |

Prepare B by completely dispersing the Carboxypolymethylene in the water and then blending in the Chlorotrifluoroethylene resin. Heat both A. and B. to 80°C. and add A. to B. with vigorous agitation. Once the mix has been blended to uniformity, cool it rapidly to 30°C. Perfume as desired when the blend reaches 50°C. A cleansing cream prepared as above has a pH of 8.1 and a viscosity of about 40,000cps (Brookfield, 20rpm). An exact viscosity determination of the system was difficult because of the thixotropic character of the composition.

EXAMPLE 8

Insect Repellent Gel:

| Components | Parts by Weight |
|---|---|
| Metadelphene | 600 |
| Ethanol (SD-40) | 100 |
| Carboxypolymethylene | 10 |
| Homopolymer of tetrafluoroethylene | 25 |
| Triethanolamine | 8 |

Disperse the carboxypolymethylene in the metadelphene. Add the triethanolamine. Add the perfluorocarbon resin. Slowly add the ethanol with mild agitation. The whole mass will slowly gel.

EXAMPLE 9

Deodorant:

| Components | Parts by Weight |
|---|---|
| Water | 90.0 |
| Carboxypolymethylene | 1 |
| Homopolymer of tetrafluoroethylene | 5.0 |
| Sodium Hydroxide (10% solution) | 1 |
| Lanolin (anhydrous) | 3 |

Disperse the carboxypolymethylene in the water and thoroughly mix. Add the resin and sodium hydroxide. Slowly mix until a cream is formed.

EXAMPLE 10

A container one quarter full of the homopolymer of tetrafluoroethylene is added to perfume oil. There if further added a flourine related compound ($ClF_3$). The container is now closed and the temperature is elevated to 50°C for about 7 days. The perfume oil is thereby pressured into the perfluorocarbon resin. Cosmetics made in this manner have a longer lasting perfume odor than is found in ordinary cosmetics.

Other preparations that may be made to include perfluorocarbon resins or chlorotrifluoroethylene resins are soaps, vanishing creams, medicated creams, skin oils, medicated ointments and salves. For example, in making bar soap, the resin is added to the soap solution, in the percentage desired, prior to coagulation.

It will be evident from the above that creams, cosmetic ointments and salves prepared in accordance with the present invention have properties which make them far more suitable than similar products containing conventional ingredients. The term "cosmetic preparations" employed herein is intended to include ointment, salves, creams, rouges, liniments, lotions, brilliantines, bar soaps, and other cosmetic preparations, of the type herein disclosed.

I claim:

1. A method of lubricating or softening the skin which comprises applying to the skin a composition comprising water, carboxypolymethylene and about 1 to about 50% by weight of a lubricating agent selected from the group consisting of chlorotrifluoroethylene resin, the homopolymer of tetrafluoroethylene, the homopolymer of hexafluoropropylene, and the copolymer of tetrafluoroethylene and hexafluoropropylene having the formula $(CF_2CF_2\text{-}CF_2CFCF_3)_n$ where n is an integer corresponding to the number of repeating units in the copolymerized chain, said lubricating agent having a particle size of between about 0.01 to about 30 microns and said composition having a pH of about 7–8.1.

2. The method of claim 1 wherein the particle size of said lubricating agent is between about 0.01 and about 0.5 microns.

* * * * *